United States Patent [19]
Berger

[11] Patent Number: 4,573,921
[45] Date of Patent: Mar. 4, 1986

[54] PROSTHESIS AND APPARATUS FOR MOLDING THE PROSTHESIS

[76] Inventor: Robert P. Berger, 4421 Rochelle Pl., Encino, Calif. 91316

[21] Appl. No.: 625,112

[22] Filed: Jun. 27, 1984

[51] Int. Cl.[4] .................. B29C 33/52; B29C 41/40
[52] U.S. Cl. ..................... 433/167; 164/DIG. 4; 164/244; 249/54; 249/62
[58] Field of Search .......... 164/244, 246, DIG. 4; 249/54, 62; 433/167, 213

[56] References Cited

U.S. PATENT DOCUMENTS

| | | | |
|---|---|---|---|
| 1,244,257 | 10/1917 | Sweetnam | 249/54 |
| 1,307,299 | 6/1919 | Laing | 249/54 |
| 1,942,981 | 1/1934 | Schmitz | 164/DIG. 4 |
| 2,065,977 | 12/1936 | Jefferies | 164/DIG. 4 |
| 3,443,627 | 5/1969 | Watts | 164/244 |
| 3,648,760 | 3/1972 | Cooper | 164/244 |
| 3,985,178 | 10/1976 | Cooper | 164/DIG. 4 |
| 4,081,019 | 3/1978 | Kulig | 164/DIG. 4 |

*Primary Examiner*—Willard E. Hoag
*Attorney, Agent, or Firm*—Allan M. Shapiro

[57] ABSTRACT

The wax master sprue and runner or gate form used in the investment casting process of dental prostheses has a web between the runners or gates so that the runners or gates are secured together to prevent shifting of the runners or gates during the molding of the casting material around the wax master.

15 Claims, 8 Drawing Figures

U.S. Patent   Mar. 4, 1986   4,573,921
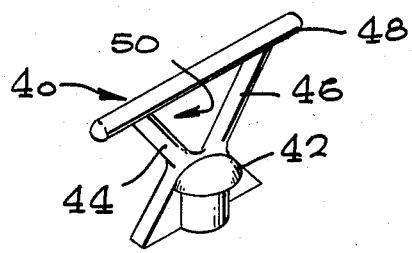
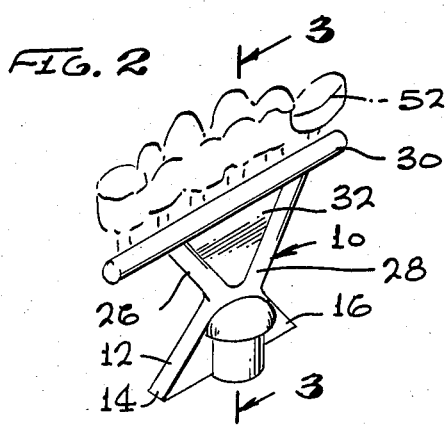
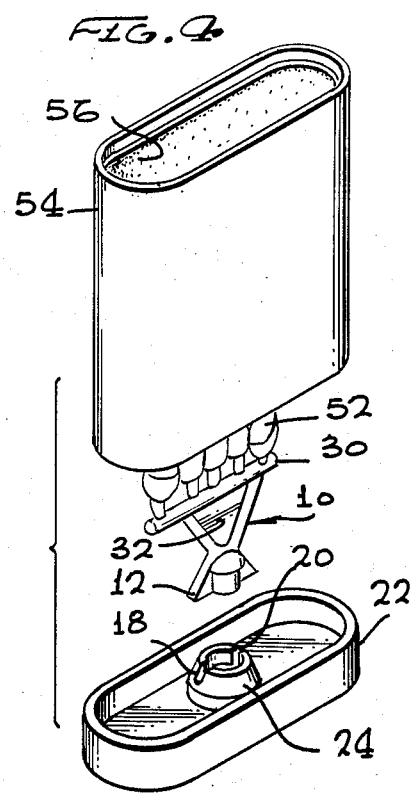
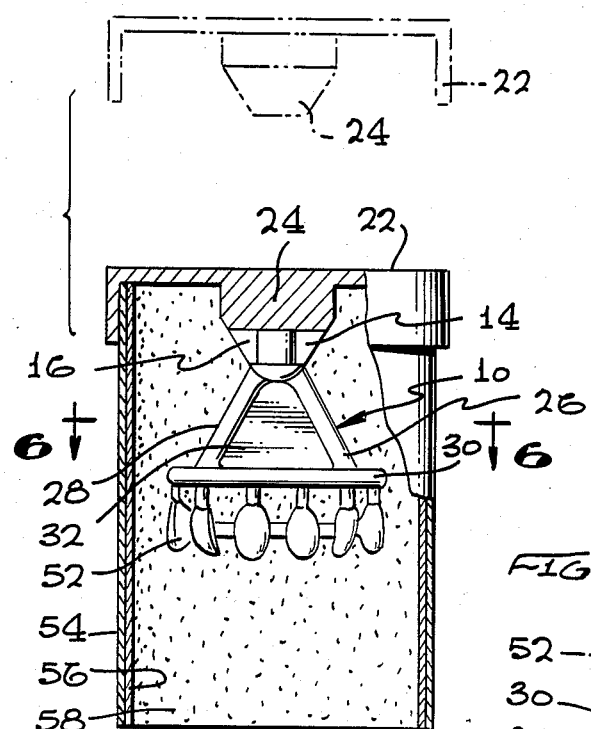
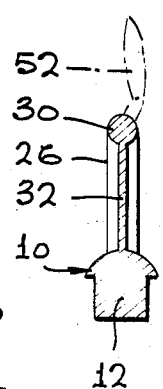
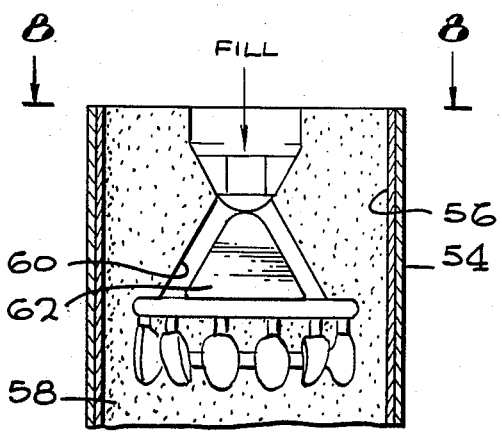
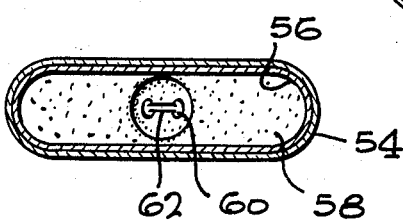
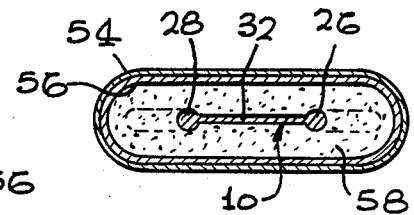

PROSTHESIS AND APPARATUS FOR MOLDING THE PROSTHESIS

BACKGROUND OF THE INVENTION

This invention is directed to a dental prosthesis restoration molding apparatus wherein the runners or gates of the wax master have a web therebetween to retain the gates in place during the forming of the mold.

The lost wax molding process has been used for centuries in the investment casting of jewelry. It comprises the formation of a wax master in the configuration of the desired final metal part, attachment of wax sprue and runners or gates to that wax master, casting investment material around the wax master, melting out the wax master, and finally pouring metal into the space previously formed in the investment material molding compound by the wax master. When the metal of the final object is hardened, the molding compound is broken away, the sprue and gates cut away, and the object is then finished as desired.

The lost wax investment casting molding process has been employed to mold dental prostheses and restorations, such as metal crowns and portions of bridges. The metals used in dentistry shrink approximately 2 percent upon solidification. Common alloys used for this purpose include nickel-chromium, palladium-gold and palladium-silver. Depending upon the alloy, these metallic alloys are poured into the investment at temperatures from 1350 to 1650 degrees Fahrenheit. These alloys generally shrink about 2 percent upon solidification. In order to accommodate this metallic shrinking upon solidification, the investment casting materials for dentistry are compounded so that they expand the cavity around the wax master by about 2 percent during the setting of the investment material. In the molding of dental prostheses which span several existing teeth, the size and shape of the finished molding must be accurately maintained.

The investment casting material is a high temperature ceramic material which is poured in liquid form around the wax master. The investment casting material goes through a plastic stage during its curing. During this plastic stage, the investment material is weak and may crack if improper stresses are placed thereon. The geometry of the wax master is important to permit setting of the investment casting material without distortion and cracks. The geometry of the sprues and gates of the prior art has led to distortion so that it has been difficult to maintain accuracy, using present-day wax molding masters.

The investment casting processes used for molding items with other purposes have employed other techniques for avoiding problems during the setting of the investment casting material. These other techniques are used in such manufacturing as the investment casting of jewelry. In such cases, an investment casting material having the property of not expanding (maintaining the cavity size) is used. This prevents cracking of the investment material during setting. To accommodate for the shrinking of the metal upon hardening, an oversized wax master is used. This cannot be done in dentistry because the wax master is derived from the actual tooth contour, spacing and arch in the patient's dentition. Thus, it is necessary to improve the accuracy of present-day wax molding masters to improve the accuracy of the finished dental prostheses molded in conjunction therewith.

SUMMARY OF THE INVENTION

In order to aid in the understanding of this invention, it can be stated in summary form that it is directed to a wax master having runners or gates for use in the lost wax molding process for dental prostheses and restorations, wherein the gates are joined by a web to retain the gates in position relative to each other to increase the accuracy of the mold made around the wax master.

It is, thus, an object and advantage of this invention to provide an improved prosthesis restoration molding apparatus wherein the prosthesis is of enhanced accuracy so as to more precisely fit the mouth for which it is intended.

It is a further object and advantage of this invention to provide a wax master sprue and gate structure for carrying a wax master prosthesis, wherein the gates are secured together to maintain the gates in position during the setting of investment casting molding compound therearound so that the mold is more accurate because the gates are held in place.

It is a further object and advantage of this invention to provide a wax master sprue and gate structure for use in investment casting of dental prostheses when the gates are connected by a web to eliminate connection in the investment casting material which would cause stresses which produce cracking or distortion of the investment casting material as it sets.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is an isometric view of the prior art wax master sprue and gate structure for use in the lost wax molding process.

FIG. 2 is an isometric view of the wax master sprue and gate in accordance with this invention, for use in the lost wax molding process, showing a wax master of a dental prosthesis in dotted lines attached thereto, which is the same as the final cast prosthesis article.

FIG. 3 is a section of the wax master sprue and gate of this invention, as seen generally along the line 3—3 of FIG. 2.

FIG. 4 is an exploded view of the wax master sprue and gate and dental prosthesis as they are placed in a mold housing for the placement of mold-forming material therearound.

FIG. 5 is an exploded view showing the mold with the wax still in place, and parts broken away and parts taken in section to show the manner in which the wax master controls the formation of a mold cavity within the molding material.

FIG. 6 is a section taken generally along the line 6—6 of FIG. 5.

FIG. 7 is a section through the mold, showing the cavity therein after the wax has been melted out, ready for the pouring in of the metal.

FIG. 8 is a section taken generally along the line 8—8 of FIG. 7.

DESCRIPTION OF THE PREFERRED EMBODIMENT

The wax master sprue and gate of the prosthesis restoration molding apparatus of this invention is generally indicated at 10 in FIGS. 2, 3, 4, 5 and 6. The wax master sprue and gate 10 has a sprue structure 12 which has wings 14 and 16 which fit in slots 18 and 20 within boss 24 in cap 22. The sprue structure 12 fits within boss 24 to form a generally conical exterior structure which will serve as a funnel-like sprue in the molding material.

Attached to sprue structure 12 are divergent gates 26 and 28. Cross gate 30 is secured to the top of the divergent gates 26 and 28. The divergent gates and cross gate surround a triangular center area. Web 32 extends across this area and joins gates 26, 28 and 30 over their entire length so as to completely close off the area between the gates which would be open in the absence of the web. As is seen in FIG. 3, web 32 is of lesser thickness than the gates, about one-quarter the thickness thereof. The gates are in the form of circular solid cylinders, and the web is defined by planes which are parallel to each other, spaced from each other, and lie on opposite sides of the center axes of all three gates. In the present instance, three gates are shown, but in the more broad sense if there are more than two divergent gates, a web is positioned in the opening between adjacent gates. Web 32 prevents continuity of the investment material between the gates through what would otherwise be an opening and serves to strengthen the gates and close off any open communication inbetween the gates.

The prior art wax master 40, shown in FIG. 1, has a similar sprue and gate structure, but lacks the web 32 in accordance with this invention. Sprue 42 carries gates 44 and 46. At the other end of each of these gates and secured thereto is transverse gate 48. Opening 50 is provided inbetween the gates. When the prior art wax master 40 is employed, the investment casting material extends through opening 50. This investment casting material grasps around the gates and provides a solid area between the gates. This solid area shrinks during setting and causes stresses on the gates which causes cracking of the investment casting material and distortion of the gates.

Upon the wax master sprue and gate structure 10 is mounted a wax master prosthesis 52. The prosthesis carries a plurality of parts, each generally representing a tooth restoration or tooth prosthesis. Each of the parts of the prosthesis is connected to the cross member or gate 30, and the parts of the wax master prosthesis may be connected together, as is well seen in FIG. 5. All connection and touchup for size, shape and positioning are done in wax at this time. While wax is described as the material employed, any material which is heat destructible or removable from the cavity is suitable. There are a number of thermoplastic and other materials suitable for this use. Wax and waxlike materials are conventionally used.

After the wax master prosthesis is put into satisfactory condition, mold housing 54 is placed into the cap. Mold housing 54 has a liner 56 therein. The mold housing is preferably of metal, and the liner is of softer material such as silicaceous or rock wool fiber paper. With cap 22 on the bottom, mold housing 54 surrounds and is spaced from the wax master prosthesis as well as the wax master sprue and gate. Thereupon, the investment casting molding compound 58 is placed in the mold. It is runs down around the wax master sprue, gate and prosthesis, and is hardened in that position.

The molding material is a high temperature ceramic, and while the apparatus of this invention is useful with the usual types of lost wax investment material, it is particularly useful with modern high temperature ceramic investment material used in dental investment casting such as crystobelite. The powder is mixed with a liquid and poured into the mold around the wax master structure. It hardens in the mold without heat and during the hardening process, it goes through a plastic stage. In reaching the plastic stage, the investment material shrinks and when it can engage all the way around the gates, the shrinkage applies radial and other forces to the gates which cause movement in the position and shape of the prosthesis. The web 32 helps hold the gates and consequently the prosthesis wax master in place during this hardening stage. Holding the gates in place is particularly necessary where the prosthesis includes caps on the ends of a bridge, such as is shown in the prosthesis 52. The end caps must be accurately placed and the arch must be of the proper shape for the prosthesis to properly fit in the mouth.

It is to be noted that the dental investment casting molding compound 58 does not enter through an opening between the gates. In the prior art, when the molding compound went through the opening 50 between the gates, the molding compound during its hardening process caused distortion of the gates which caused movement of transverse gate 48 and the wax master prosthesis mounted thereon. The result was changes in configuration between the original wax master prosthesis and the mold cavity derived therefrom. The forces of the molding compound on the wax master gates cause this repositioning of the parts of the prosthesis. The placement of the web 32 so that it completely prevents the molding compound from closing around the divergent gates and cross gates prevents this source of distortion. In addition, the web 32 provides lateral strength in the direction of the gates toward and away from each other, rather than present a situation of unsupported gates 44, 46 and 48. By the use of the web 32 connecting to the adjacent gates and completely prevently any through engagement of the molding compound provides the positioning strength.

After the molding compound is set, cap 22 is removed from the full line to the dotted line position of FIG. 5, and the mold housing 54 with its contents is turned over. Thereupon, the entire structure is heated so that the wax melts out. After the wax is melted out, there is a cavity 60 into which the metal of the prosthesis structure will be poured. The sprue at the top provides a funnel-like structure to receive the hot metal. As seen in FIGS. 7 and 8, the cavity 60 includes a flat cavity section or slit 62 into which a metallic web is cast with the rest of the casting process. The cavity includes the prosthesis molding section at the lower portion of FIG. 7, and this prosthesis section has been held accurately in place during the formation of the mold cavity during the formation of the cavity. Accordingly, the prosthesis is accurately positioned.

After the metal is poured into the mold and is cooled, the molding compound is thrust axially out of the mold housing. The mold liner 56 provides the freedom for ease of removal of the molding compound with the metal therein. When removed, the molding compound is broken away from the metal prosthesis and gates. The prosthesis is further finished by cutting away the gates, final shaping, ceramic coating and sintering, or whatever conventional prosthesis making requires. Thus, an accurate prosthesis is produced.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A heat destructible pattern for use in forming a mold for a prosthesis, comprising:
a heat destructible substantially central member corresponding to a gate of the mold;
at least two spaced destructible elongated runner members connected with said substantially central member for forming runners between said substantially central member and a mold cavity; and
a destructible web connected to both said elongated destructible members substantially throughout their entire length, said destructible web being thinner than said destructible runner members.

2. The pattern of claim 1 wherein said substantially central member, said elongated runner members and said web are made of wax-like material to form a gate and runners in an investment casting mold.

3. The pattern of claim 1 wherein said two elongated destructible runner members are divergent and a cross runner member is joined with said elongated runner members in a position opposite said central member for forming a cross runner member joining said runner members, said web being attached to all of said runner members.

4. The pattern of claim 1 wherein at least two runner members are connected together adjacent said central member, said two runner members being positioned to be diverging, a cross runner member interconnecting said two divergent runner members adjacent their divergent ends, said web being attached to all three said runner members to close substantially all space between said runner members in a direction at right angles to said web to inhibit investment material flow between said runner members.

5. The pattern of claim 1 wherein said web is less than half the thickness of said runner members.

6. The pattern of claim 1 wherein there is a heat destructible master of a dental prosthesis attached to said cross runner member so that said cross runner member and said wax master of a dental prosthesis are held in place by said runner members and said web during the positioning of molding material and hardening of molding material around said runner members and heat destructible master dental prosthesis.

7. The pattern of claim 3 wherein said runner members are of circular cross section and said web is positioned to prevent the molding material from wrapping around said runner members to preclude substantial forces on said runner members from said molding material.

8. The pattern of claim 3 wherein said runner members are of substantially the same diameter and are of substantially uniform diameter and thickness of said web is less than about half the diameter of said runner members.

9. A mold for a prosthesis, comprising:
a mold mass having a cavity therein, said cavity comprising walls defining a substantially central gate in said mold;
at least two spaced elongated runners connected with said central member;
a slit in said central cavity interconnecting said runners substantially throughout their length, said slit being of lesser thickness than said runner.

10. The mold of claim 9 wherein said elongated runners are divergent and there is a cross runner joining said divergent runners in a position away from said central gate, said slit being open to all of said runners to form a slit extending between all the runners of said mold.

11. The mold of claim 10 wherein said runners are connected to said central gate adjacent each other and said runners diverge away from said central gate, a cross runner connected to both of said divergent runners away from said central gate, said slit being connected to all three of said runners.

12. A molded article comprising:
a substantially central mold gate;
at least two elogated runners connected to said substantially central gate; and
a web connected to said runners substantially throughout their length, said web being thinner than said runners.

13. The article of claim 12 wherein said runners are divergent away from said substantially central gate and a cross runner is joined with both of said divergent runners in a position away from said central gate, said web being attached to all of said runners.

14. The article of claim 12 wherein said two runners are connected to said substantially central gate adjacent each other and said two runners diverge in a direction position away from said substantially central gate and a cross runner is connected to both of said divergent members away from said substantially central gate, said web being attached to said three runners to substantially close all opening between said runners viewed in a direction normal to said web.

15. The article of claim 14 further including a dental prosthesis attached to said cross runner.

* * * * *